United States Patent [19]
Schreiber

[11] Patent Number: 5,176,654
[45] Date of Patent: Jan. 5, 1993

[54] METHOD AND APPARATUS FOR OTOLOGIC ADMINISTRATION OF MEDICAMENT

[76] Inventor: Simeon B. Schreiber, 1214 N. Belgrade Rd., Silver Spring, Md. 20902

[21] Appl. No.: 623,769

[22] Filed: Dec. 7, 1990

[51] Int. Cl.$^5$ ............................................... A61M 5/00
[52] U.S. Cl. ..................................... 604/181; 604/187
[58] Field of Search .................... 604/181, 187, 218; 239/330, 331, 333, DIG. 12, DIG. 19; 222/385, 383

[56] References Cited

U.S. PATENT DOCUMENTS

| | | | |
|---|---|---|---|
| 660,212 | 10/1900 | Ertsman | 604/181 |
| 1,354,641 | 10/1990 | Zietlow . | |
| 1,493,592 | 5/1924 | Beck | 604/181 |
| 1,903,681 | 4/1933 | Merliss | 604/181 |
| 2,188,190 | 1/1940 | Moos | 604/181 |
| 2,249,832 | 7/1941 | Hubschman . | |
| 2,392,085 | 1/1946 | Ferrel | 239/DIG. 19 |
| 2,710,711 | 6/1955 | Hutton | 604/181 |
| 2,786,718 | 3/1957 | Middlestadt | 239/333 |
| 3,207,387 | 9/1965 | Brickman | 222/400.8 |
| 3,398,743 | 8/1968 | Shalit | 604/181 |
| 3,625,213 | 12/1971 | Brown . | |
| 3,640,470 | 2/1972 | Susuki et al. | 239/333 |
| 3,666,182 | 5/1972 | Cureton . | |
| 3,991,914 | 11/1976 | Kotuby et al. | 239/333 |
| 4,056,216 | 11/1977 | Kotuby | 222/385 |
| 4,691,849 | 9/1987 | Tada | 239/333 |
| 4,830,284 | 5/1989 | Maerte | 239/333 |
| 4,995,867 | 2/1991 | Zollinger | 604/218 |

OTHER PUBLICATIONS

Murine ® ear wax removal system, *Physicians' Desk Reference*, 1991 Edition, pp. 1911–1912.

*Primary Examiner*—Paul J. Hirsch

[57] ABSTRACT

The present invention is an apparatus for the delivery of a fluid substance, such as a medicament, in a spray form to the ear of a user comprising a fluid receptacle, a pump, a delivery tube bent at an angle of approximately 90° and a nozzle which is dimensioned to prevent damage to the external organs of the ear when introduced therein.

18 Claims, 2 Drawing Sheets

METHOD AND APPARATUS FOR OTOLOGIC ADMINISTRATION OF MEDICAMENT

FIELD OF THE INVENTION

The present invention relates to an apparatus for the delivery of fluid substances, such as medicaments, into body cavities. More particularly the invention is an apparatus for the delivery of medicaments to the ear which is configured to prevent damage to the exterior organs of the ear when introduced therein.

BACKGROUND OF THE INVENTION

Presently, fluid substances or medicaments are administered to the ear using a standard fluid "dropper" device. Although the dropper has become widely accepted as a satisfactory means for administering medicaments to the external canal or meatus, use of the dropper for this procedure is often difficult and dangerous. It is especially difficult to administer ear medicine to children via the dropper device unless they are able to maintain their head in a relatively still position.

If during the administration of medicine to the ear the tip of the dropper device is inserted into the ear canal too deeply, the tip may pierce the tympanic membrane or abrade the inner wall of the ear canal. Thus, with regard to children, it is critical that their head remain completely still while the dropper is proximate the ear, since any movement may force the dropper into damaging contact with even the inner ear. Furthermore, due to the length of the typical conduit, the dropper does not allow the hand of the user to rest against the patient's head for support. Therefore, when administering ear medicine to children, because the user cannot safely rely on the child's ability to remain still, the child must be horizontally positioned or the user must enlist the assistance of another individual to maintain the position of the child.

Moreover, the dropper device dispenses medicine in droplet form which flows into the ear canal along the lower wall only. Thus, the upper and side walls or surfaces of the ear canal are not exposed to the medicament and the treatment may be incomplete. In addition, the dispensing of medicament in droplet form does not assure the administration of a complete and accurate dosage of ear medicament. If the correct dosage of ear medicament is not achieved initially, the user must administer additional doses, frequently wasting a substantial amount of medicament.

Furthermore, utilization of the dropper device involves possible contamination risks. If the dropper tip comes into direct contact with the ear infection, the dropper becomes contaminated and, unless disposed of, further contaminates the fluid medicament when returned to the fluid receptacle.

One example of a standard ear medicine dropper is the Murine Ear Wax Removal System/Murine Ear Drops described in the 1984 edition of Physician's Desk Reference. Although the description recommends that the tip of the dropper not enter the ear canal, the degree of tip penetration is ultimately controlled by the user. Therefore, even the slightest, unexpected head movement could force the dropper tip into damaging contact with the tympanic membrane. Furthermore, the Murine device requires that the head of the patient be tilted sideways for effective administration of medicine.

Other devices which attempt to overcome the disadvantages of Murine-type droppers are well known in the art. One example of such a device is disclosed in U.S. Pat. No. 1,354,641 to Zietlow. The Zietlow patent offers a solution to the dispensing of medicaments in droplet form by utilizing a combined atomizer and vaporizer to disperse medicine to the entire interior surface of a body cavity. The Zietlow patent discloses a combined atomizer and vaporizer which includes a receptacle and a horizontally positioned atomizing tube. A second tube, which telescopically fits over the atomizing tube, is provided with a nasal engaging nozzle to direct liquid or vapor into the nasal passages. However, the Zietlow device requires the use of both hands, leaving no hand free to steady the head of the user. Also, the length of the vaporizing tube places the apparatus at a distance from the user's head which does not allow support from the hands to prevent head movement. Moreover, the nozzle of the Zietlow device is constructed particularly for use with the nose and therefore is not configured to prevent damage to the exterior ear organs.

Another example of a device structured to overcome the disadvantages of a dropper is disclosed in the Brown patent, U.S. Pat. No. 3,625,213. The Brown patent discloses a device for dispensing medicaments into body cavities such as the ear or nose which includes a flexible capsule, a support member and a conduit which is reduced in diameter to readily project into a body cavity for fluid application. While the Brown conduit readily projects into the body cavity, it is not structured to prevent excessive penetration which may damage the external organs of the ear canal. Furthermore, for use with the ear, the Brown device must be inverted or the user's head must be tilted.

Still another device which seeks to improve upon the fluid dropper is disclosed in, for example, U.S. Pat. No. 3,666,182 to Cureton. The Cureton patent discloses a squeeze bottle for emitting a horizontal spray comprised of nozzle. The neck portion is positioned so that the user need not invert the bottle or tilt his head. However, the Cureton device must be turned to an angle of 90° to achieve emittance of a horizontal spray. Furthermore, the nozzle portion of the Cureton device is not dimensioned to prevent deep penetration into the ear canal which may damage the external ear organs.

Moreover, none of the above-described devices reliably delivers an accurate and complete dosage of ear medicament to the ear of the user.

Thus, the need exists for an ear spray apparatus which reliably administers an accurate dosage of medicament to the ear canal while minimizing the possibility of injury to the external ear organs. The need also exists for an ear spray device which leaves one of the user's hands free to steady the head or to prevent head movement which could cause injury to the ear.

SUMMARY OF THE INVENTION

In accordance with the above-described objectives, the present invention is an apparatus for the delivery of fluid substances, such as medicaments, to an ear comprising a receptacle for receiving a fluid substance; a pump disposed within the receptacle for drawing a predetermined amount of fluid out of the receptacle and delivering the predetermined fluid in a spray form to the ear; a delivery tube for delivering the fluid from the pump to the ear, the tube having a distal end and proximal end, the proximal end of which is secured to the pump; and a nozzle having an ear end or first portion and a tube end or second portion, the tube end of which is fitted to the distal end of the delivery tube and the ear end of which dispenses fluid from the tube to the external ear. The ear end of the nozzle is specifically dimensioned to prevent damage to the external organs of the ear when introduced into the ear.

The nozzle of the apparatus may be removable and may be constructed of plastic or rubber. The ear end of the nozzle may be of a diameter smaller than that of the tube end and may be of the shape of a truncated cone. Furthermore, the ear end of the nozzle may be of a diameter larger than that of the tube end and may be of the shape of a mushroom. The nozzle may also be provided with an interior conduit. Moreover, the delivery tube of the apparatus may be bent at an angle of approximately 90°.

Furthermore, the present invention is an apparatus for the delivery of fluid substances, such as medicaments, to an ear comprising a receptacle for receiving the fluid substance; a pump disposed within the receptacle for drawing a predetermined amount of fluid out of the receptacle and delivering the predetermined fluid in a spray form to the ear; a delivery tube bent at an angle of approximately 90° having a distal end and a proximal end, the proximal end of which is secured to the pump; and a nozzle having a ear end and a tube end, the tube end of which is fitted to the distal end of the delivery tube.

The nozzle of the apparatus may be removable and may be constructed of plastic or rubber. The ear end of the nozzle may be of a diameter smaller than that of the tube end and may be of the shape of a truncated cone. Furthermore, the ear end of the nozzle may be of a diameter larger than that of the tube end and may be of the shape of a mushroom. The nozzle may also be provided with an interior conduit. Moreover, the pump of the apparatus may be provided with a fore and middle finger actuator.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which.

DETAILED DESCRIPTION OF THE DRAWINGS

Figure 1:
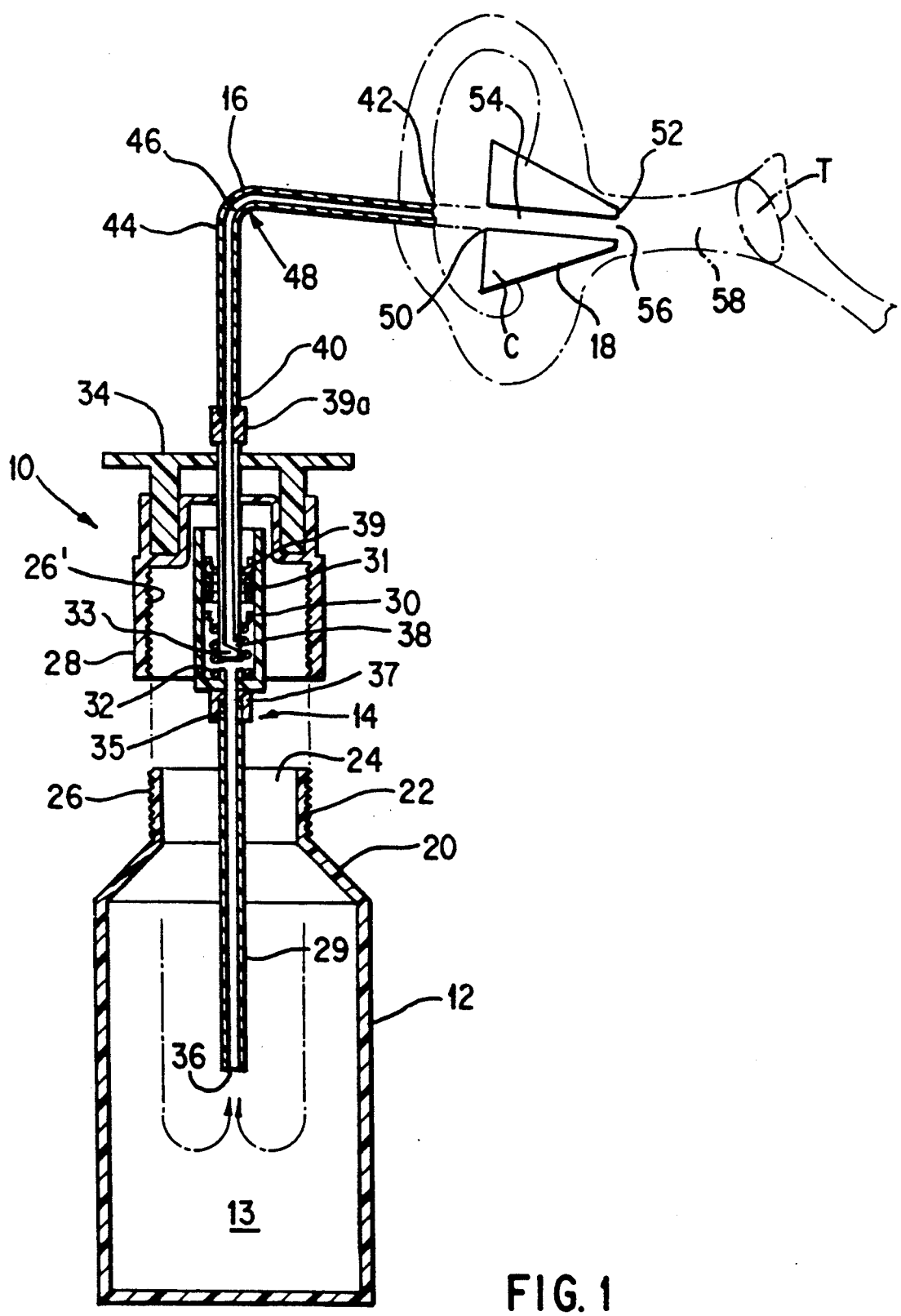
FIG. 1 is an exploded longitudinal cross-sectional view of the ear spray apparatus of the present invention.

With continuing reference to the drawing figures in which similar reference numerals are used throughout the description to describe similar features of the invention, the apparatus of the present invention is shown generally at 10 in FIG. 1. The apparatus comprises a fluid receptacle 12, a pump 14, a fluid delivery tube 16 and a nozzle 18, each of which will now be described in greater detail.

With continuing reference to FIG. 1, fluid receptacle 12 is shown having a generally rectangular cross-section, the walls of which create a hollow reservoir 13 for the containment of fluid. At its upper portion 20, receptacle 12 is provided with a neck 22 which forms a cylindrical opening 24. Neck 22 of receptacle 12 is threaded, as at 26, to removably secure similarly threaded pump 14. The receptacle may be constructed of plastic or any other suitable material which is chemically compatible with chosen medicament to assure maintenance of drug stability. Furthermore, receptacle 12 may be of any shape which is easily received within the hand of the user.

Fluid receptacle 12 is in fluid communication with pump 14. As shown in FIG. 1, a partially actuated pump 14 is inserted within fluid receptacle 12 through opening 24. Cap 28, having threads 26', threadably engages with neck 22 of fluid receptacle 12 to secure pump 14 within receptacle 12.

Pump 14 is provided with a hollow fluid suction tube 29, a fluid chamber 30, an actuating spring 31, a biasing spring 32, a plunger 33 and a fore and middle finger actuator 34, each of which will now be described in greater detail.

Fluid suction tube 29 is hollow and includes a proximal end 35 and a distal end 36. Proximal end 35 of tube 29 is securingly engaged with the remainder of the pump mechanism at 37, while distal end 36 is suspended within reservoir 13 of fluid receptacle 12. In a preferred embodiment, fluid suction tube 29 has an outer diameter of approximately four millimeters, an inner diameter of two millimeters and is approximately four centimeters in length. However, the inner diameter may be of any dimension which allows an ear suspension or liquid/particle medicament, such as NEOMYCIN POLYMYXIN/HC, to travel easily therethrough. Fluid suction tube 29 may be constructed of plastic or other suitable material which is chemically compatible with the chosen medicament. Proximal end 35 opens into fluid chamber 30, the walls of which form a reservoir which contains a predetermined amount of fluid. A plunger 33, comprised of a hollow tube having an aperture 38 disposed at its lower side, is received within fluid chamber 30 and is surrounded by an actuating spring 31 at its upper end and a biasing spring 32 at its lower end. Plunger 33 is provided with a annular shoulder 39 located superior to actuating spring 31. A fore and middle finger actuator 34 is disposed superior to fluid chamber 30 and is in direct communication with plunger 33.

The pump of the present invention operates in the following manner. The pump mechanism is placed within fluid receptacle 12 and is secured thereto by threading means 26 and 26'. Initially, atmospheric pressure force fluid contained within the fluid receptacle up into fluid chamber 30 through suction tube 36. The pump is actuated by applying an external downward force upon fore and middle finger actuator 34. Actuator 34, which is in direct communication with plunger 33, pushes plunger 33 through actuating spring 31 into fluid chamber 30. As annular shoulder 39 comes into contact with actuating spring 31, spring 31 compresses to limit the distance in which plunger 33 may protrude into chamber 30. The high pressure created within fluid chamber 30 by plunger 33, forces fluid to enter the interior portion of plunger 33 (an area of lower pressure) through aperture 38 and travel therethrough into delivery tube 16 which is connected thereto by a connecting means 39a. When the external force upon fore and middle finger actuator 34 is removed, actuating spring 31 decompresses and plunger 33 exits the fluid chamber. The release of the high pressure caused by plunger 33 forces fluid within receptacle 12 (now under high pressure) to flow (by suction, shown as dashed arrows in FIG. 1) through suction tube 29 into fluid chamber 30 to refill the same. Thus, the pump of the present invention draws a predetermined amount of fluid from fluid receptacle 12 and delivers it to the remainder of apparatus 10. Furthermore, the pump of the present invention is designed to reliably deliver an exact amount of the fluid each time the pump is actuated. Examples of pumps suitable for use with the present invention include the pump mechanisms utilized with commercially available nasal spray medicines such as NASALIDE and VANCENASE AQ.

With continuing reference to FIG. 1, delivery tube 16 is hollow and includes a proximal end 40 and a distal end 42. Proximal end 40 is securingly engaged to pump 14 by a suitable connector means 39a. Delivery tube 16 has an outer diameter of approximately four millimeters, an inner diameter of approximately two millimeters and is approximately eight centimeters in length. However, the inner diameter may be of any dimension which allows the ear suspension or medicament to travel easily therethrough. The tube may be constructed of plastic or other suitable material which is chemically compatible with ear medicaments. At an appropriate midpoint 44, delivery tube 16 is bent at an angle of approximately 90° to allow apparatus 14 to be introduced to the ear while receptacle 12 is in an upright or vertical position. It should be noted, however, that delivery tube 16 may be bent at any other suitable angle which allows the apparatus to be introduced to the ear without invertion of fluid receptacle 12. Furthermore, the tube may be bent at any other point along its length which, when introduced to the ear, places the apparatus at a distance which allows the user's actuating hand to provide support to the head. At midpoint 44, or at any other point where the tube is bent, the inner diameter of the tube may be slightly increased, as at 46, to prevent blockage of the suspension (a fluid/particle solution as previously described) or medicament when passing through bent portion 48 of tube 16.

Distal end 42 of delivery tube 16 is fitted with a removable truncated cone-shaped nozzle 18. One example of a suitable cone-shaped nozzle is that utilized with a nasal atomizer manufactured by DeVilbiss of Sommerset, Pa. Throughout its length, nozzle 18 is provided with a cylindrical interior conduit 54 into which tube 16 is partially received. Interior conduit 54 is of a diameter slightly greater than that of the outer diameter of tube 16 and allows fluid medicament to pass therethrough into the ear.

Nozzle 18 is has a first portion or ear and 52 having a first diameter and a second portion or tube end 50 having a second diameter. First diameter of first portion 52 is dimensioned to allow nozzle 18 to fit easily and snugly within the ear concha C. Second diameter of second portion 50 is dimensioned to prevent first portion 52 from entering entrance 56 of ear canal 58 preventing damage thereto. As shown in FIG. 1, ear end 52 of nozzle 18 is of a diameter smaller than that of tube end 50. In its preferred form, nozzle 18 is approximately 2.5 centimeters in length, ear end portion 52 is approximately eight millimeters in diameter and tube end 50 is approximately 2.3 centimeters in diameter. Nozzle 18 is specifically configured to prevent damage to the external ear organs when introduced into the ear. Nozzle 18 may be of any length and combination of diameters which prevents penetrating the ear canal so deeply as to risk puncture of tympanic membrane T (shown in phantom). As shown in FIG. 1, ear end 52 is prevented by the diameter of tube end 50 from extending beyond the entrance 56 of ear canal 58 (shown in phantom). Therefore, there is no possibility of damage to the external ear organs. Moreover, the relative diameters of nozzle 18 allows it to be snugly received within the concha C or outer ear (shown in phantom). Thus, nozzle 18 is supported by the outer ear and is afforded minimal relative movement which could result in external ear damage.

Nozzle 18 is preferably constructed of a relatively hard plastic or rubber or any other suitable material which is chemically compatible with ear medicine, biocompatible with the body, and is unyielding to external pressure. The nozzle 18 may be disposable for single use or sterilizable for multiple use.

Figure 2:
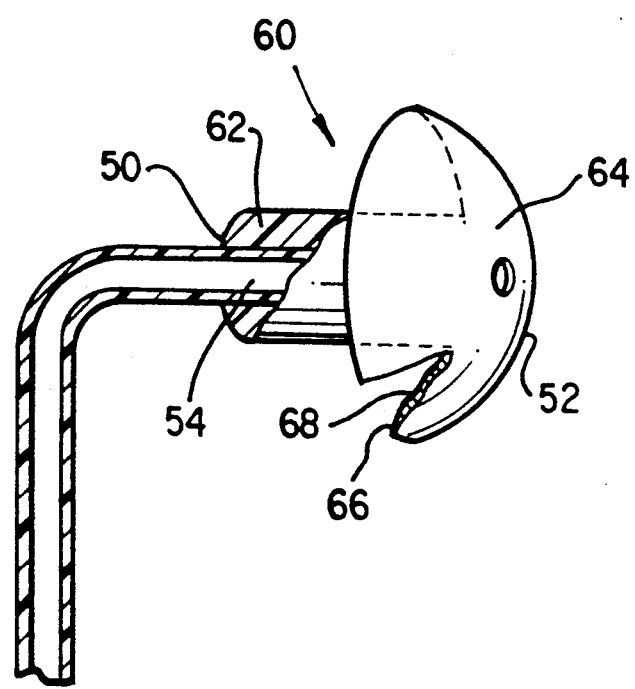
FIG. 2 is a partial cut-away view of an alternate embodiment of a nozzle for the ear spray apparatus shown in FIG. 1.

An alternate embodiment of the nozzle shown in FIG. 1 is shown in FIG. 2 as a mushroom-shaped nozzle 60 which is available from Grason-Stadler Inc. as a means for introducing air or sound to the tympanic membrane. Nozzle 60 also has a first portion or ear end 52 having a first diameter and a second portion or tube end having a second diameter. Similar to the embodiment shown in FIG. 1, first diameter of first portion 52 is dimensioned to allow nozzle 18 to fit easily and snugly within the ear concha C. Second diameter of second portion 50 is dimensioned to prevent first portion 52 from entering entrance 56 of ear canal 58 preventing damage thereto. Tube end 50 is cylindrical in shape, while ear end 52 is shaped as a convex disk. An interior conduit 54 passes through nozzle 50 from tube end 50 to ear end 52. The diameter of interior conduit 54 is slightly greater than that of delivery tube 16 and allows fluid medicament to pass therethrough.

First diameter of ear end 52 is greater than second diameter of tube end 50 second diameter of second portion 50 is greater than the inner diameter of the ear canal entrance 56 (FIG. 1). Tube end 50 includes cylindrical wall 62 which is preferably approximately 1.5 millimeters thick and is constructed of a relatively inflexible plastic or rubber material. However, the walls may be constructed of any other suitable material which is relatively inflexible, sterilizable, and chemically compatible with the selected medicament and the body. Ear end 52 is preferably two centimeters in diameters and is preferably constructed of the same material as tube end 50. However, because of its reduced thickness, it is more flexible than tube end 50. The exterior surface 64 of ear end 52 is convex to be easily received within the ear concha C (FIG. 1). The periphery 66 of interior surface 68 is beveled to provide increased flexibility which will allow ear end 52 to snugly fit within the concha affording minimal relative movement of the nozzle 60. It should be realized that regardless of the degree of penetration by ear end 52, nozzle 60 cannot enter the ear canal due to the relative inflexibility and diameter of tube end 50. That is, the diameter of tube end 50 is too large to enter the ear canal. Thus, damage to the external ear organs is virtually impossible.

Both nozzle 18 and 60 may be constructed for adult or pediatric use. Of course, the dimensions of the respective nozzles will be dictated by the diameter of the adult or pediatric external ear canal.

The present invention is easily utilized in the following manner. Using the right or left hand, the user grasps the fluid receptacle and places his fore and middle finger on the pump actuator extensions. The apparatus is then brought to the ear, in its upright position, and the nozzle is inserted completely into the ear concha. The user's hand automatically supports the head by resting on the side of the patient's face. The other hand is free to the patient's head. With the head steadied the pump is actuated and a predetermined amount or metered dose of medicine is sprayed to all surfaces of the ear canal. The apparatus is then removed from the ear, and the nozzle is removed for disposal or sterilization to prevent contamination.

The invention which is intended to be protected herein should not be construed as limited to the particular forms disclosed, as these are to be regarded as illustrative rather than restrictive. Variations and changes may be made by those skilled in the art without departing from the spirit of the invention. Accordingly, the foregoing detailed description should not be considered exemplary in nature and not limited to the scope and spirit of the invention as set forth in the attached claims.

What is claimed is:

1. An apparatus for the delivery of fluid substances, such as medicaments, to an ear comprising:
    a receptacle for receiving a fluid substance;
    a pump in fluid communication with said receptacle for delivering said fluid substance in a spray form to an ear;
    a delivery tube for delivering said fluid substance from said pump to said ear, said delivery tube having a distal end and a proximal end, said proximal end secured to said pump; and
    a fluid nozzle secured to said distal end of said delivery tube, said fluid nozzle having a first portion having a first diameter dimensioned to allow said nozzle to fit easily and snugly within the concha of said ear, and a second portion having a second diameter dimensioned to prevent said first portion of said fluid nozzle from entering the canal of said ear;
    whereby when said nozzle is introduced into said ear, said fluid nozzle is prevented from damaging the external organs of said ear.

2. An apparatus as set forth in claim 1, wherein said delivery tube is bent at an angle of 90°.

3. An apparatus as set forth in claim 1, wherein said fluid nozzle is removable.

4. An apparatus as set forth in claim 1, wherein said first diameter of said fluid nozzle is smaller than said second diameter.

5. An apparatus as forth in claim 4, wherein said fluid nozzle is in the shape of a truncated cone.

6. An apparatus as forth in claim 5, wherein said fluid nozzle is constructed of rubber.

7. An apparatus as set forth in claim 5, wherein said fluid nozzle is constructed of plastic.

8. An apparatus as set forth in claim 1, wherein said fluid nozzle is provided with an interior conduit.

9. An apparatus as set forth in claim 1, wherein said first diameter of said fluid nozzle is greater than said second diameter.

10. An apparatus as set forth in claim 9, wherein said fluid nozzle is in the shape of a mushroom.

11. An apparatus as set forth in claim 10, wherein said fluid nozzle is rubber.

12. An apparatus as set forth in claim 10, wherein said fluid nozzle is plastic.

13. An apparatus as set forth in claim 1, wherein said pump is provided with a fore and middle finger actuator.

14. An apparatus as set forth in claim 1, wherein said first diameter and said second diameter are dimensioned to be received within the ear of a child.

15. An apparatus as set forth in claim 1, wherein said pump draws a predetermined amount of fluid substance out of said receptacle and delivers said predetermined amount of fluid substance to said ear.

16. A method for delivering fluid substances to an ear comprising the steps of:
    providing a medicament in a fluid receptacle having a pump which delivers fluid in a spray and a fluid nozzle having a first portion having a first diameter dimensioned to allow said fluid nozzle to fit easily and snugly within the concha of said ear, and a second portion having a second diameter dimensioned to prevent said first portion of said fluid nozzle from entering the canal of said ear to prevent damage thereto;
    inserting said fluid nozzle in the ear concha so that said fluid nozzle fits easily and snugly within the concha of said ear but does not enter the ear canal;
    actuating said pump to thereby deliver a spray of medicament to the surface of the ear canal; and
    removing said fluid nozzle from said ear.

17. The method of claim 16, further including the step of removing said fluid nozzle from said fluid receptacle for disposal or sterilization of said fluid nozzle following said step of removing said fluid nozzle from said ear.

18. The method of claim 16, wherein a predetermined amount of fluid substance is delivered to said ear.

* * * * *

US005176654B1

REEXAMINATION CERTIFICATE (3947th)

United States Patent [19]
Schreiber

[11] B1 5,176,654
[45] Certificate Issued Dec. 7, 1999

[54] METHOD AND APPARATUS FOR OTOLOGIC ADMINISTRATION OF MEDICAMENT

[76] Inventor: Simeon B. Schreiber, 1214 N. Belgrade Rd., Silver Spring, Md. 20902

Reexamination Request:
No. 90/004,975, Apr. 23, 1998

Reexamination Certificate for:
Patent No.: 5,176,654
Issued: Jan. 5, 1993
Appl. No.: 07/623,769
Filed: Dec. 7, 1990

[51] Int. Cl.⁶ .................................................. A61M 5/00
[52] U.S. Cl. ................................. 604/181; 604/187
[58] Field of Search ............................ 604/181, 187, 604/218; 239/330, 331, 333, DIG. 12, DIG. 19; 222/383, 386

[56] References Cited

U.S. PATENT DOCUMENTS

| | | | |
|---|---|---|---|
| D. 89,947 | 2/1933 | Cohn | D24/106 |
| D. 191,088 | 8/1961 | Anderson | D24/112 |
| D. 238,006 | 12/1975 | Anderson | D24/112 |
| 2,430,229 | 11/1947 | Kelsey | 381/338 |
| 2,441,866 | 5/1948 | Cantor | 128/867 |
| 3,776,362 | 12/1973 | Rice | 181/135 |
| 3,820,698 | 6/1974 | Franz | 222/208 |
| 3,901,233 | 8/1975 | Grossan | 604/215 |
| 4,206,756 | 6/1980 | Grossan . | |

OTHER PUBLICATIONS

Grossan, M., "Cerumen Removal—Current Challenges," ENT Journal 1998; 77(7):541–42, 44–46 and 48.

*Primary Examiner*—Paul J. Hirsch

[57] ABSTRACT

The present invention is an apparatus for the delivery of a fluid substance, such as a medicament, in a spray form to the ear of a user comprising a fluid receptacle, a pump, a delivery tube bent at an angle of approximately 90° and a nozzle which is dimensioned to prevent damage to the external organs of the ear when introduced therein.

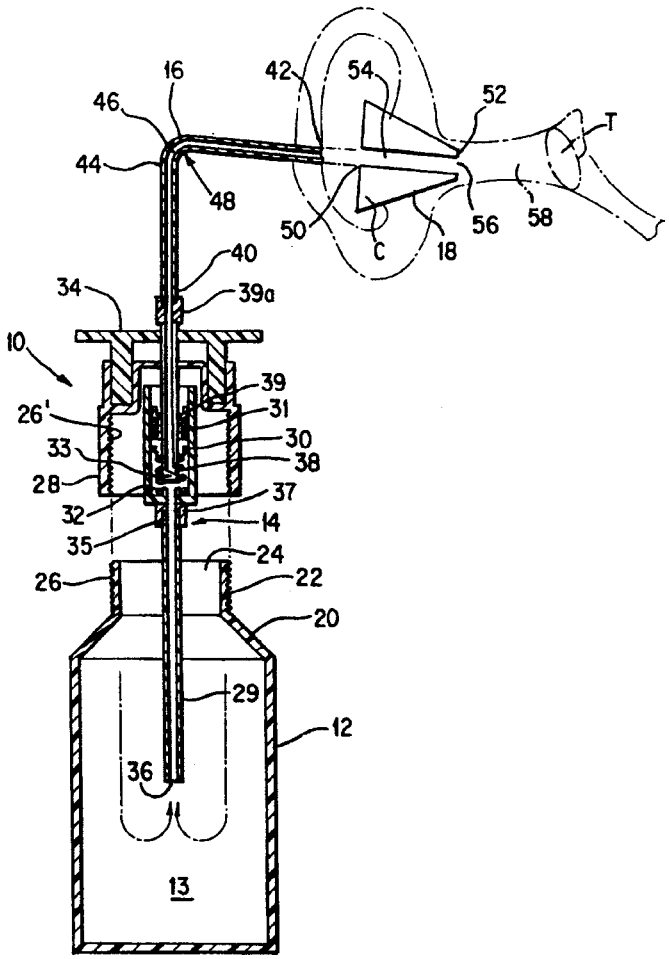

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–18 is confirmed.

* * * * *